United States Patent [19]
Schulz et al.

[11] Patent Number: 6,037,482
[45] Date of Patent: Mar. 14, 2000

[54] PROCESS FOR CATALYTIC ADDITION OF NUCLEOPHILES TO ALKYNES OR ALLENES

[75] Inventors: Michael Schulz; Joaquim Henrique Teles, both of Ludwigshafen, Germany

[73] Assignee: BASF Aktiengesellschaft, Ludwigshafen, Germany

[21] Appl. No.: 09/091,235

[22] PCT Filed: Dec. 6, 1996

[86] PCT No.: PCT/EP96/05457

§ 371 Date: Jun. 15, 1998

§ 102(e) Date: Jun. 15, 1998

[87] PCT Pub. No.: WO97/21648

PCT Pub. Date: Jun. 19, 1997

[30] Foreign Application Priority Data

Dec. 13, 1995 [DE] Germany .......................... 195 46 610

[51] Int. Cl.$^7$ ................................................. C07D 319/12
[52] U.S. Cl. .......................... 549/377; 549/430; 568/409; 568/594; 568/672; 568/678; 568/690; 568/695; 568/892; 568/898

[58] Field of Search ..................................... 568/408, 409, 568/594, 672, 678, 688, 689, 690, 695, 895, 898, 892; 549/377, 378, 379, 430

[56] References Cited

PUBLICATIONS

Journal of Organic Chemistry by Fuduka et al. 56 pp. 3729–3731 1991.

JAPIO1992–095039 abs of JP04095039 by Yukitoshi.

*Primary Examiner*—Gary Geist
*Assistant Examiner*—Jean F Vollano
*Attorney, Agent, or Firm*—Oblon, Spivak, McClelland, Maier & Neustadt, P.C.

[57] ABSTRACT

A process for the catalytic addition of nucleophilic agents to alkynes or allenes to form alkenes substituted by the nucleophile which may further react with the nucleophile and/or isomerize comprises using a catalyst comprising a wholly or partly ionized complex of univalent gold.

9 Claims, No Drawings

PROCESS FOR CATALYTIC ADDITION OF NUCLEOPHILES TO ALKYNES OR ALLENES

DESCRIPTION

The present invention relates to a process for the addition of nucleophiles to alkynes and allenes in the presence of a wholly or partly ionized complex of univalent gold applicable to a wide range of alkynes and allenes.

The addition of nucleophiles to alkynes is catalyzed by acids, bases or transition metal complexes (cf. Houben-Weyl, Methoden der organischen Chemie, Vol. 6/3, p. 233, p. 90, Vol. 5/2a, p. 738, Vol. 6/1d, p. 136 and Vol. 7/a, p. 816).

The acid catalysis is usually restricted to the addition of nucleophiles to activated, electron-rich alkynes (such as acetylene ethers, R—C≡C—OR', acetylene thioethers, R—C≡C—SR' and acetyleneamines, —C≡C—NR'$_2$).

Alcohols can be added to unactivated alkynes by base catalysis (in the presence of KOH or alcoholate). This is the method of choice for the monoaddition of alcohols to alkynes to form enol ethers.

The addition of nucleophiles to alkynes is also catalyzed by transition metal complexes. Generally, they are complexes of metals of groups 11 and 12 (according to the currently applicable IUPAC nomenclature of inorganic chemistry). Rhodium, ruthenium, palladium and platinum catalysts have also been used in individual cases.

According to J. S. Reichert, H. H. Bailey, J. A. Nieuwland, J. Am. Chem. Soc., 45 (1923), 1552, and G. F. Hennion, J. A. Nieuwland, J. Am. Chem. Soc., 57 (1935), 2006, mercury(II) compounds, usually in combination with a Lewis and a Brbnsted acid, are the most active catalysts for the addition of nucleophiles to alkynes. Such Hg(II) catalysts can be used to add water, alcohols and carboxylic acids to alkynes. These catalysts have very general utility, but their scope of application is limited by the toxicity of mercury and by the relatively low turnover numbers (<500), ie. the ratio of the number of moles of product formed per mole of catalyst.

W. Reppe, Ann., 601 (1956), 81, describes zinc(II) and cadmium(II) compounds for use as catalysts for the addition of carboxylic acids and phenols to alkynes.

Gold(III) compounds such as sodium tetrachloroaurate (NaAuCl$_4$) have hitherto been described for use as catalysts for the addition of water or alcohols to alkynes only once (Y. Fukuda, K. Utimoto, J. Org. Chem., 56 (1991), 3729).

Gold(I) compounds have evidently hitherto not been used as ctalysts for the addition of nucleophiles to alkynes.

As can be seen from the description of the background art, there are numerous existing processes for the addition of nucleophiles to alkynes, but they all have a limited range of applications. The hitherto preferred mercury catalysts, in particular, have the disadvantage of toxicity and relatively low turnover numbers, so that a high catalyst consumption had to be tolerated or appreciable amounts of byproducts were formed.

It is an object of the present invention to propose a universally useful catalytic process for the addition of nucleophilic agents to alkynes or allenes and, more particularly such a process as does not have the disadvantages described and which even makes possible the addition of weak nucleophiles and the addition to unactivated alkynes.

We have found that this object is achieved according to the invention by a process for the catalytic addition of nucleophilic agents to alkynes or allenes to form alkenes substituted by the nucleophile which may further react with the nucleophile and/or isomerize, which comprises using a catalyst comprising a wholly or partly ionized complex of univalent gold.

Since the complexes have to be at least partly present in ionized form, it is assumed that the catalytic effect is due to a complex cation of the formula 1

where the ligand L can represent the building blocks

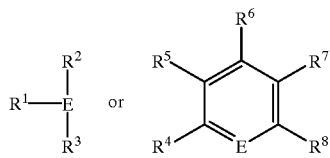

and where

R$^1$, R$^2$ and R$^3$ independently of the others represent substituted or unsubstituted aliphatic, cycloaliphatic, aromatic, heteroaromatic or araliphatic radicals having from 1 to 30 carbon atoms which may be bridged and may optionally be attached to E via an oxygen atom or via a nitrogen atom, E is phosphorus, arsenic or antimony, and R$^4$, R$^5$, R$^6$, R$^7$ and R$^8$ are each hydrogen or a substituted or unsubstituted aliphatic, cycloaliphatic, aromatic, heteroaromatic or araliphatic radical having from 1 to 30 carbon atoms, a corresponding alkoxy group or ester group or alternatively a nitro group, cyano group or halogen, and the ligand L can also have been incorporated into a polymer.

Accordingly, the catalysts used are in particular complexes of the formula 2

where the ligand L is as defined above and X is an anion, especially a weakly coordinating or noncoordinating anion.

The process of the present invention is of particular importance for the addition of water, alcohols having from 1 to 30 carbon atoms or carboxylic acids having from 1 to 30 carbon atoms to alkynes having from 2 to 60 carbon atoms or to allenes having from 3 to 60 carbon atoms in the presence of a catalyst of the formula 2a

where

R$^1$, R$^2$ and R$^3$ are substituted or unsubstituted alkyl, cycloalkyl, aryl or aralkyl radicals having in each case from 1 to 30, preferably from 1 to 10, carbon atoms, which may be bridged and may each be attached to E via an oxygen atom or via a nitrogen atom, E is arsenic, antimony or especially phosphorus, and X is an anion, especially a weakly coordinating or non-coordinating anion.

Preference is given to complexes of the formula 2a where the radicals $R^1$, $R^2$ and $R^3$ are substituted or unsubstituted primary, secondary or tertiary alkyl radicals or substituted or unsubstituted aryl radicals such as pyridyl, naphthyl or in particular phenyl radicals or substituted or unsubstituted alkoxy or aryloxy radicals.

Coordinating anions for the purposes of this invention include for example chloride, bromide and iodide; weakly coordinating anions include for example nitrate, sulfate, azide, cyanate, sulfonates such as tosylate, methanesulfonate, trifluoromethanesulfonate, sulfinates such as -benzenesulfinate, alkoholates such as methanolate, ethanolate or -2,2,2-trifluoroethanolate, phenolate, carboxylates such as acetate or -trifluoroacetate; and noncoordinating anions include for example perchlorate, tetrafluoroborate, hexafluoroantimonate, hexafluorophosphate or tetraphenylborate.

The process of the present invention performs particularly well when the catalyst used has the formula 2a where X is a weakly coordinating or uncoordinating anion selected from the group consisting of nitrate, sulfate, azide, sulfonate, sulfinate, alcoholate, phenolate, carboxylate, perchlorate, tetrafluoroborate, hexafluoroantimonate, hexafluorophosphate and tetraphenylborate.

The aforementioned catalytically active ionized gold(I) complexes are generally not stable in the free form and are therefore generally prepared in situ. Several well known methods are available for this in the examples which follow L is always as defined above):

1. In situ reaction of a stable gold(I) complex of the formula 3 where R' is alkyl, cycloalkyl, alkenyl, alkynyl, aralkyl or aryl, with a Brönsted acid HY, where Y is a weakly coordinating or noncoordinating anion, or with a Lewis acid, especially with $BF_3$ as etherate or methanolate.

4. Dissolution of a stable gold(I) complex of the formula 3

$$L-AuX \quad (3),$$

where X is a radical capable of forming an anion, in a polar medium in which the complex can dissociate into free or solvated ions.

Similarly, any other reaction whereby the cation of the formula 1 can be generated in situ is suitable.

The ionized gold(I) complexes of the formula 2 to be used as catalysts and their starting compounds of the formulae 3 and 4 are known from the literature, for example from D. I. Nichols and A.S. Charleston, J. Chem. Soc. (A) (1969), 2581, U.S. Pat. No. 3,661,959, and Inorganic Synthesis 26 (1989) 325, hereby cited for reference.

Suitable nucleophilic agents, or nucleophiles for short, for the novel catalyzed addition to alkynes or allenes are the well known agents capable of electron donation. Suitable compounds include in particular water, alcohols having from 1 to 30, preferably from 1 to 10, carbon atoms, such as methanol, ethanol, 2-propanol or t-butanol, phenols, carboxylic acids having from 1 to 20, preferably from 1 to 10, carbon atoms, such as formic acid, acetic acid or acrylic acid, thiols, sulfonic acid, phosphoric acids, hydrogen halides or else compounds containing a combination of the functionalities mentioned.

Suitable alkynes or allenes for the nucleophilic addition of the invention are any compounds having, respectively, from 2 to 60 and 3 to 60 carbon atoms. However, preference is given to alkynes or allenes having respectively from 2 to 8 and from 3 to 8 carbon atoms and alkynes having functional groups. Examples of suitable starting materials include accordingly preferably alkynes (terminal or internal) from acetylene through octyne, allene, propargyl alcohol, 1-butyn-3-ol or 2-butyne-1,4-diol.

The addition of the nucleophilic agents, for example methanol, to an alkyne is effected in a conventional manner according to the following scheme:

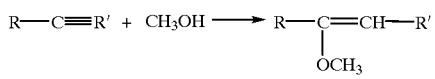

The resulting enol ether generally adds a further molecule of methanol to form the compound

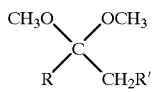

In the case of the addition of water the enol then immediately forms the corresponding ketone by isomerization. Also possible are further reactions with ring formation, as shown below. These reactions are all known and not a particular feature of the present process.

In what follows, some additions catalyzed according to the invention are recited to exemplify possible applications.

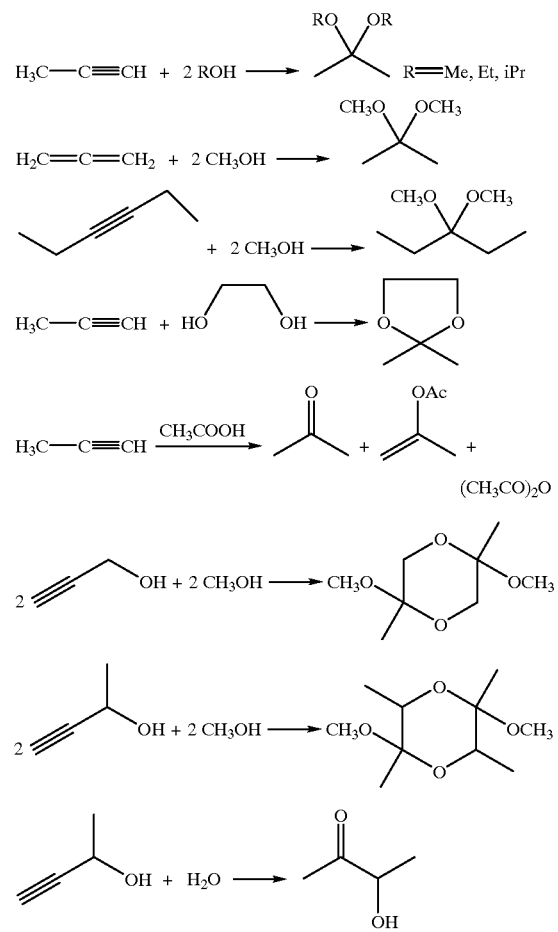

-continued

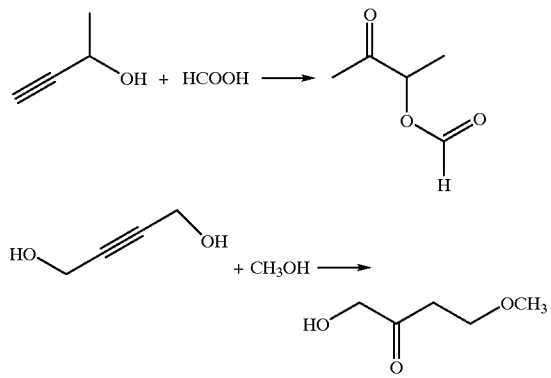

The addition catalyzed according to the invention can be carried out not only in the presence but also in the absence of an inert solvent. Preference is given to the procedure without solvent, ie. using the nucleophile and/or the alkyne as reaction medium.

The molar ratio of nucleophile to alkyne or allene can be chosen within the range from 0.01 to 10000. Preference is given to ratios within the range from 0.9 to 100. Particular preference is given to ratios within the range from 1 to 5.

The reaction temperature is within the range from −30 to +150° C., preferably within the range from 0 to 80° C. Particular preference is given to temperatures within the range from 20 to 60° C.

The addition can be carried out at atmospheric pressure, reduced pressure and elevated pressure.

The molar ratio between the gold(I) complex, which is used in deficiency, and the sum of the reactants can be chosen within the range from 0.1 to $10^{-8}$. Preference is given to ratios within the range from 0.01 to $10^{-5}$. The gold(I) complex is not consumed during the addition reaction and can be recovered from the reactor effluent after the reaction product has been distilled and recycled into the reaction stage, so that the reaction can also be carried out continuously. Excellent turnover numbers are obtained, even at low conversion in a single pass, since virtually no byproducts are formed and the process is thus notable for high selectivity. Finally, the gold(I) complex catalyst is stable under the reaction conditions, whereas, for example, the gold(III) complexes mentioned in the introductory part of this description tend to shed gold and hence to form a mirror of gold on the reactor surfaces.

EXAMPLES

The starting compounds for the catalysts were each prepared according to literature methods.

Examples 1 to 13
Addition of Methanol to Propyne Using L—Au—X+Lewis Acid (method 1)

In a flask equipped with gas inlet tube, thermometer and reflux condenser, methanol (39.6 g, 1235 mmol) was provided, heated to 40° C. and presaturated with propyne. The gold(I) complex (0.062 mmol Au) shown in Table 1 and BF$_3$ etherate (0.62 mmol) were then rapidly added in succession. During the reaction time, a slow stream of propyne was passed into the reaction mixture. Table 1 shows the concentration of 2,2-dimethoxypropane (DMP) reached after six hours (h). Apart from 2,2-dimethoxypropane, no other products were detected; that is, the reaction proceeds with excellent selectivity.

TABLE 1

| Example | Gold (I) catalyst | DMP concentration [wt. %] |
|---------|-------------------|---------------------------|
| 1 | Ph$_3$PAu(NO$_3$) | 42 |
| 2 | (4-F-Ph)$_3$PAu(NO$_3$) | 44 |
| 3 | Ph$_2$(C$_6$F$_5$)PAu(NO$_3$) | 47 |
| 4 | Et$_3$PAu(NO$_3$) | 24 |
| 5 | Ph$_3$AsAu(NO$_3$) | 32 |
| 6 | Ph$_3$PAu(OOCCF$_3$) | 42 |
| 7 | Ph$_3$PAu(OOCCF$_3$)*) | 13 |
| 8 | Ph$_3$PAuCl | 0.7 |
| 9 | Ph$_3$PAuI | 0.2 |
| 10 | Ph$_3$PAuCH$_3$ | 40 |
| 11 | (Ph$_3$PAu)$_3$O$^+$BF$_4^-$ | 40 |
| 12 | (PhO)$_3$PAu(NO$_3$) | 32 |
| 13 | (CH$_3$O)$_3$PAu(NO$_3$) | 48 |

*)reaction at 20° C.
Ph = Phenyl
Et = Ethyl

Example 14
Addition of Ethanol to Propyne Using L—Au—X+Lewis Acid (method 1)

In a flask equipped with gas inlet tube, thermometer and reflux condenser, ethanol (11.4 g, 245 mmol) was provided, heated to 60° C. and presaturated with propyne. Triphenylphosphine gold(I) chloride (0.062 mmol) and BF$_3$ etherate (0.62 mmol) were then added in rapid succession. During the reaction time, a slow stream of propyne was passed into the reaction mixture. After a reaction time of 3 h the reaction mixture comprised 21.6% by weight of 2,2-diethoxypropane and 0.8% by weight of 2-ethoxypropene. Apart from 2,2-diethoxypropane and 2-ethoxypropene no other products were detected.

Example 15
Addition of Isopropanol to Propyne Using L—Au—R+Brönsted Acid (method 3)

In a flask equipped with gas inlet tube, thermometer and reflux condenser, isopropyl alcohol (148.5 g, 2475 mmol) was provided, heated to 40° C. and presaturated with propyne. Triphenylphosphine gold(I) methyl (59 mg, 0.124 mmol) and methanesulfonic acid (125 mg, 1.3 mmol) were then added in rapid succession. During the reaction time, a slow stream of propyne was passed into the reaction mixture. After 6 h the reaction mixture comprised 2.4% by weight of 2-isopropoxypropene and 1.9% by weight of 2,2-diisopropoxypropane as the only products detectable.

Example 16
Addition of Allyl Alcohol to Propyne Using L—Au—X+Lewis Acid (method 1)

In a flask equipped with gas inlet tube, thermometer and reflux condenser, allyl alcohol (143.6 g, 2472 mmol) was provided, heated to 40° C. and presaturated with propyne. Triphenylphosphine gold(I) nitrate (0.064 g, 0.124 mmol) and BF$_3$ etherate (1.3 mmol) were then added in rapid succession. During the reaction time, a slow stream of propyne was passed into the reaction mixture. After 4 h the reaction mixture comprised 28% of acetone diallyl ketal as the only detectable product.

Example 17
Addition of Acetic Acid to Propyne Using L—Au—X+Lewis Acid (method 1)

In a flask equipped with gas inlet tube, thermometer and reflux condenser, acetic acid (9.61 g, 160 mmol) was provided, heated to 60° C. and presaturated with propyne.

Triphenylphosphine gold(I) chloride (0.04 mmol) and $BF_3$ etherate (0.4 mmol) were then added in rapid succession. During the reaction time, a slow stream of propyne was passed into the reaction mixture. After a reaction time of 4 h the reaction mixture comprised 12.9% by weight of acetone. Acetic anhydride is formed as coproduct.

Example 18

Addition of Acetic Acid to Propyne Using L—Au—X+ Lewis Acid (method 1)

In a flask equipped with gas inlet tube, thermometer and reflux condenser, acetic acid (74.2 g, 1235 mmol) was provided, heated to 40° C. and presaturated with propyne. Triphenylphosphine gold(I) trifluoroacetate (0.062 mmol) and $BF_3$ etherate (0.62 mmol) were then added in rapid succession. During the reaction time, a slow stream of propyne was passed into the reaction mixture. After a reaction time of 5 h the reaction mixture comprised 3.5% by weight of isopropenyl acetate and 1.0% by weight of acetone. Acetic anhydride was detected as coproduct.

Example 19

Addition of Methanol to Propyne Using L—Au—X (method 4)

In a flask equipped with gas inlet tube, thermometer and reflux condenser, methanol (7.91 g, 245 mmol) was provided, heated to 60° C. and presaturated with propyne. Triphenylphosphine gold(I) trifluoroacetate (0.062 mmol) was then added. During the reaction time, a slow stream of propyne was passed into the reaction mixture. After a reaction time of 1 h the reaction mixture comprised 3.8% by weight of 2,2-dimethoxypropane. Apart from 2,2-dimethoxypropane no other products were detected.

Example 20

Addition of Methanol to Propyne Using L—Au—X+Ag Salt (method 2)

In a flask equipped with gas inlet tube, thermometer and reflux condenser, methanol (39.55 g, 1235 mmol) was provided, heated to 40° C. and presaturated with propyne. Triphenylphosphine gold(I) chloride (0.062 mmol) and silver hexafluoroantimonate were then added in rapid succession. During the reaction time, a slow stream of propyne was passed into the reaction mixture. After a reaction time of 6 h the reaction mixture comprised 4.0% by weight of 2,2-dimethoxypropane. Apart from 2,2-dimethoxypropane no other products were detected.

Examples 21 to 26

Addition of Methanol to Propyne Using L—Au—R'+Brönsted Acid (method 3)

In a flask equipped with gas inlet tube, thermometer and reflux condenser, methanol (79.2 g, 2470 mmol) was provided, heated to 40° C. and presaturated with propyne. Triphenylphosphine gold(I) methyl (58.8 mg, 0.124 mmol), the amount evident from Table 2 of the acids evident from Table 2 were then added in rapid succession. During the reaction time, a slow stream of propyne was passed into the reaction mixture. The concentrations of 2,2-dimethoxypropane (2,2-DMP) and 2-methoxypropene (2-MP) reached after a reaction time of 6 h are reported in Table 2.

Apart from the products of value, 2,2-dimethoxypropane and 2-methoxypropene, only minor amounts of 1,1-dimethoxypropane (less than 0.3%) were detectable as byproduct, ie. the reaction proceeds with excellent selectivity.

TABLE 2

| Example | Brönsted acid | Amount of acid [equiv. based on Au] | 2,2-DMP concentration [wt. %] | 2-MP concentration [wt. %] |
|---|---|---|---|---|
| 21 | $HBF_4$ (54% strength in $Et_2O$) | 10 | 44 | 1 |
| 22 | $CH_3SO_3H$ | 2 | 33 | 0.5 |
| 23 | $CH_3SO_3H$ | 5 | 45 | 2 |
| 24 | $CH_3SO_3H$ | 10 | 52 | 1 |
| 25 | $CH_3SO_3H$ | 25 | 53 | 10 |
| 26 | $CH_3SO_3H$ | 100 | 52 | 21 |

Example 27

Addition of Methanol to 3-hexyne Using L—Au—X+Lewis Acid (method 1)

In a flask equipped with thermometer and reflux condenser, methanol (39.6 g, 1235 mmol) and 3-hexyne (25.32 g, 309 mmol) were provided and heated to 40° C. Triphenylphosphine gold(I) nitrate (0.062 mmol) and $BF_3$ etherate (0.62 mmol) were then added in rapid succession. After 22 h the reaction mixture comprised 57.7% by weight of 3,3-dimethoxyhexane, 2.2% by weight of 3-hexanone and 5.6% by weight of an isomer mixture of 3-methoxyhexene. Apart from the products mentioned no other products were detected.

Example 28

Addition of Methanol to Propargyl Alcohol Using L—Au—R+Brönsted Acid (method 3)

In a three-neck flask equipped with thermometer and reflux condenser, methanol (94.5 g, 2.95 mol) and propargyl alcohol (41.35 g, 0.738 mol) were provided and heated to 40° C. Triphenylphosphine gold(I) methyl (3.5 mg, 7.35 μmol) and methanesulfonic acid (17.5 mg, 184 μmol) were then added in rapid succession. After 23 h at 40° C. about 98% of the propargyl alcohol had reacted (this corresponds to 98,000 turnovers). The main product formed was a mixture of the two isomers 2,5-dimethoxy-2,5-dimethyl-1,4-dioxane (in a ratio of 5:1) together with small amounts of hydroxyacetone and hydroxyacetone dimethyl ketal. Following partial removal of the methanol, the product crystallized in the form of large colorless crystals (44.5 g, corresponding to 69% of theory, isolated yield, mp.=126° C., literature mp.=126–128° C).

Example 29

Addition of Methanol to Propargyl Alcohol Using L—Au—X+Lewis Acid (method 1)

In a flask equipped with thermometer and reflux condenser, methanol (39.6 g, 1235 mmol) and propargyl alcohol (11.54 g, 206 mmol) were provided and heated to 40° C. Triphenylphosphine gold(I) nitrate (0.062 mmol) and $BF_3$ etherate (0.62 mmol) were then added in rapid succession. After 4 h the reaction mixture was cooled down to room temperature, causing 2,5-dimethyl-2,5-dimethoxy-1,4-dioxane (9.83 g, 55 mmol, 54% yield) to come down as a colorless powder (melting point: 126 to 128° C., Lit.: 127° C.).

Example 30

Addition of Methanol to 2-butyne-1,4-diol Using L—Au—X+Lewis Acid (method 1)

In a flask equipped with thermometer and reflux condenser, methanol (39.6 g, 1235 mmol) and 2-butyne-1,4-diol (17.73 g, 206 mmol) were provided and heated to 40° C. Triphenylphosphine gold(I) nitrate (0.062 mmol) and BF$_3$ etherate (0.62 mmol) were then added in rapid succession. After 6 h all the butynediol had reacted. The products were 4-methoxy-2-keto-butan-1-ol (90% yield), hydroxymethyl vinyl ketone (5% yield) and 2-keto-butane-1,4-diol (5% yield).

Example 31

Addition of Methanol to 2-butyne-1,4-diol Using L—Au—R+Brönsted Acid (method 3)

In a three-neck flask equipped with thermometer and reflux condenser, methanol (154 g, 4.8 mol) and 2-butyne-1,4-diol (103.2 g, 1.2 mol) were provided and heated to 40° C. Triphenylphosphine gold(I) methyl (102.6 mg, 216 μmol) and methanesulfonic acid (0.72 g, 7.2 mmol) were then added in rapid succession. After 24 h at 40° C. about 99% of the 2-butyne-1,4-diol had reacted (this corresponds to 5500 turnovers). The methanesulfonic acid was then neutralized by addition of sodium methanolate and the methanol was then removed in a rotary evaporator. The residue (yellowish liquid, 127 g, corresponding to about 80% yield) was more than 90% 1-hydroxy-4-methoxybutan-2-one according to GC. The product is only distillable with considerable losses (bp.: 56–57° C./4 mbar).

Example 32

Addition of Water to 1-butyn-3-ol Using L—Au—X+Lewis Acid (method 1)

In a flask equipped with a thermometer and reflux condenser, 50 g of a 55% strength aqueous solution of 1-butyn-3-ol (393 mmol of butynol, 1250 mmol of water) were provided and heated to 60° C. Triphenylphosphine gold(I) nitrate (0.062 mmol) and BF$_3$ etherate (0.62 mmol) were then added in rapid succession. After 5 h 3-hydroxybutan-2-one (acetoin, yield about 6%) had formed as the only product.

Example 33

Addition of Water to Propargyl Alcohol with L—Au—R+Brönsted Acid (method 3)

In a three-neck flask equipped with thermometer and reflux condenser, propargyl alcohol (41.4 g, 0.74 mol) and triphenylphosphine gold(I) methyl (3.5 mg, 74 μmol) were provided and heated to 80° C. Methanesulfonic acid (472 μl, 7.35 mmol) dissolved in water (53.2 g, 2.95 mol) was then added. After 1.5 h at 80° C. the solution comprised 1.5% by weight of hydroxyacetone as sole product.

Example 34

Addition of Methanol to but-3-yn-2-ol Using R$_3$E—Au—X+Lewis Acid (method 1)

In a flask equipped with thermometer and reflux condenser, methanol (39.6 g, 1235 mmol) and anhydrous 1-butyn-3-ol (23.8 g, 309 mmol) were provided and heated to 60° C. Triphenylphosphine gold(I) nitrate (0.062 mmol) and BF$_3$ etherate (0.62 mmol) were then added in rapid succession. After 6 h about 50% of the 1-butyn-3-ol had reacted. The products formed were 2,3,4,5-tetramethyl-2,5-dimethoxy-1,4-dioxane (92%, as diastereoisomer mixture), 2,3,4,5-tetramethyl-2-methoxy-1,4-diox-2-ene (5%) and 2,2-dimethoxy-butan-3-ol (3%).

Example 35

Addition of Formic Acid to 1-butyn-3-ol using L—Au—X+Lewis Acid (method 1)

In a flask equipped with thermometer and reflux condenser, 1-butyn-3-ol (23.8 g, 309 mmol) and formic acid (28.4 g, 617 mmol) were provided and heated to 40° C. Triphenylphosphine gold(I) nitrate (0.031 mmol) and BF$_3$ etherate (0.62 mmol) were then added in rapid succession. After 6 h 97% of the butynol had reacted. The products formed were 3-hydroxy-2-butanone formate (89%) and 3-hydroxy-2-butanone (acetoin, 3%). About 8% of 2,3-diformyloxy-1-butene were detected as a further byproduct.

Example 36

Addition of Formic Acid to 1-butyn-3-ol Using L—Au—X+Lewis Acid (method 1)

In a flask equipped with dropping funnel, thermometer and reflux condenser, formic acid (184 g, 4 mol) and a portion of the butynol (3.86 g, 0.05 mol) were provided and heated to 50° C. Triphenylphosphine gold(I) nitrate (5.2 mg, 0.01 mmol) and BF$_3$ etherate (0.1 mmol) were then added in rapid succession. The remaining butynol (72.24 g, 0.95 mol) was then added dropwise over 2 h. The mixture was then stirred at 50° C. for a further 5 h. After this period, the butynol conversion was 82% (correspondig to 82,000 turnovers). The 2-hydroxybutan-3-one formate (acetoin formate) selectivity was 95%. The acetoin formate was obtainable in pure form by distillation of the reaction effluent (bp.: 53° C./15 mbar).

Example 37

Addition of Methanol to Acetylene Using L—Au—R+Brönsted Acid (method 3)

In a flask equipped with gas inlet tube, thermometer and reflux condenser, methanol (79.2 g, 2470 mmol) was provided, heated to 55° C. and presaturated with acetylene. Triphenylphosphine gold(I) ethyl (58.8 mg, 0.124 mmol) and methanesulfonic acid (12.4 mmol) ere then added in rapid succession. During the reaction time a slow stream of acetylene was passed into the reaction mixture. After a reaction time of 4 h the reaction solution comprised 1.5% by weight of 1,1-dimethoxyethane as sole product.

Example 38

Addition of Methanol to Phenylacetylene Using L—Au—R+Brönsted Acid (method 3)

In a flask equipped with thermometer and reflux condenser, methanol (8.01 g, 250 mmol) and phenylacetylene (6.38 g, 62.5 mmol) were provided and heated to 40° C. Triphenylphosphine gold(I) methyl (14.8 mg, 31.2 μmol) and methanesulfonic acid (40.6 μl, 625 μmol) were then added in rapid succession. After a reaction time of 8 h, 99% of the phenylacetylene had been converted. The main products formed were α-methoxystyrene (selectivity (S)=61%) and acetophenone dimethyl ketal (S=20%). Subsequent acid-catalyzed reaction of the α-methoxystyrene by-produced 1-methoxy-1,3-diphenylbutadiene (as 1:1 cis/trans mixture, S=13%) acetophenone (S=4%) and 1,3,5-triphenylbenzene (S=2%).

Example 39

Addition of Methanol to Diphenylacetylene (tolan) Using L—Au—R+Brönsted Acid (method 3)

In a flask equipped with thermometer and reflux condenser, methanol (108.1 g, 3.37 mol) and tolan (15.0 g, 84.3 mmol) were provided and heated to 40° C. Triphenylphosphine gold(I) methyl (20.0 mg, 42 μmol) and methanesulfonic acid (54.8 μl, 840 μmol) were then added in rapid succession. After a reaction time of 20 h 35% of the tolan had been converted. The only product formed was 1-methoxy-1,2-diphenylethene (as E/Z mixture, about 1:2).

We claim:

1. A process for the catalytic addition of nucleophilic agents selected from the group consisting of water, alcohols having from 1 to 30 carbon atoms, carboxylic acids having from 1 to 30 carbon atoms, and compounds containing a combination of alcohol and carboxylic acid groups to alkynes or allenes thereby forming alkenes substituted by the nucleophile which may further react with the nucleophile and/or isomerize, which comprises using a catalyst comprising a wholly or partly ionized complex of univalent gold containing a complex cation of formula (1)

 (1)

wherein the ligand L represents a building block of the formula

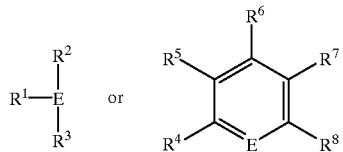

and

R$^1$, R$^2$ and R$^3$, each independently of the other, represent a substituted or unsubstituted aliphatic, cycloaliphatic, aromatic, heteroaromatic or araliphatic radical having from 1 to 30 carbon atoms which may be bridged and may optionally be attached to E via an oxygen atom or via a nitrogen atom;

E is phosphorus, arsenic or antimony;

R$^4$, R$^5$, R$^6$, R$^7$ and R$^8$ are each, independently, hydrogen or a substituted or unsubstituted aliphatic, cycloaliphatic, aromatic, heteroaromatic or araliphatic radical having from 1 to 30 carbon atoms, a corresponding alkoxy group or ester group, a nitro group, a cyano group or a halogen.

2. A process as claimed in claim 1, wherein nucleophiles are added to alkynes having from 2 to 60 carbon atoms or to allenes having from 3 to 60 carbon atoms in the presence of a catalyst of the formula 2

 (2)

wherein the ligand L represents a building block of the formula

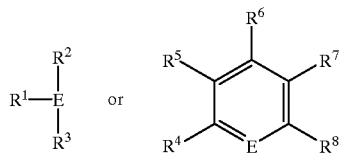

and

R$^1$, R$^2$ and R$^3$, each independently of the other, represent a substituted or unsubstituted aliphatic, cycloaliphatic, aromatic, heteroaromatic or araliphatic radical having from 1 to 30 carbon atoms which may be bridged and may optionally be attached to E via an oxygen atom or via a nitrogen atom;

E is phosphorus, arsenic or antimony;

R$^4$, R$^5$, R$^6$, R$^7$ and R$^8$ are each, independently, hydrogen or a substituted or unsubstituted aliphatic, cycloaliphatic, aromatic, heteroaromatic or araliphatic radical having from 1 to 30 carbon atoms, a corresponding alkoxy group or ester group, a nitro group, a cyano group or a halogen, and X is an anion.

3. A process as claimed in claim 2, wherein water, alcohols having from 1 to 30 carbon atoms or carboxylic acids having from 1 to 30 carbon atoms are added to alkynes having from 2 to 20 carbon atoms or allenes having from 3 to 20 carbon atoms in the presence of a catalyst of the formula 2a

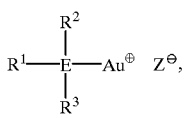 (2a)

where

R$^1$, R$^2$ and R$^3$ are alkyl or aryl radicals having from 1 to 10 carbon atoms, which may be substituted or unsubstituted and may each be attached to E via an oxygen atom, E is phosphorus, and Z is a weakly coordinating or noncoordinating anion.

4. A process as claimed in claim 3, wherein the catalyst used has the formula 2a where Z is a weakly coordinating or noncoordinating anion selected from the group consisting of nitrate, sulfate, azide, sulfonate, sulfinate, alcoholate, phenolate, carboxylate, perchlorate, tetrafluoroborate, hexafluoroantimonate, hexafluorophosphate and tetraphenylborate.

5. A process as claimed in claim 1, wherein the catalyst is formed in situ in the reaction mixture.

6. A process as claimed in claim 1, wherein the catalyst is formed in situ by reacting, with a Lewis acid, a neutral gold(I) complex of the formula 3

 (3), wherein the ligand L represents a building block of the formula

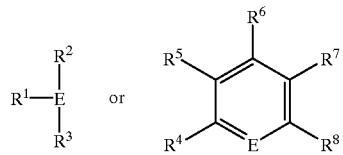

and

R$^1$, R$^2$ and R$^3$, each independently of the other, represent a substituted or unsubstituted aliphatic, cycloaliphatic, aromatic, heteroaromatic or araliphatic radical having from 1 to 30 carbon atoms which may be bridged and may optionally be attached to E via an oxygen atom or via a nitrogen atom;

E is phosphorus, arsenic or antimony;

R$^4$, R$^5$, R$^6$, R$^7$ and R$^8$ are each, independently, hydrogen or a substituted or unsubstituted aliphatic, cycloaliphatic, aromatic, heteroaromatic or araliphatic radical having from 1 to 30 carbon atoms, a corresponding alkoxy group or ester group, a nitro group, a cyano group or a halogen, and X is a radical that forms an anionic complex with said Lewis acid.

7. A process as claimed in claim 1, wherein the catalyst is formed in situ by reacting a neutral gold(I) complex of the formula 3

 L—AuX (3), wherein the ligand L represents a building block of the formula

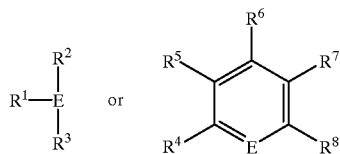

and

R$^1$, R$^2$ and R$^3$, each independently of the other, represent a substituted or unsubstituted aliphatic, cycloaliphatic, aromatic, heteroaromatic or araliphatic radical having from 1 to 30 carbon atoms which may be bridged and may optionally be attached to E via an oxygen atom or via a nitrogen atom;

E is phosphorus, arsenic or antimony;

R$^4$, R$^5$, R$^6$, R$^7$ and R$^8$ are each, independently, hydrogen or a substituted or unsubstituted aliphatic, cycloaliphatic, aromatic, heteroaromatic or araliphatic radical having from 1 to 30 carbon atoms, a corresponding alkoxy group or ester group, a nitro group, a cyano group or a halogen, and X is a Cl, Br or I, with a silver salt containing a noncoordinating anion.

8. A process as claimed in claim 1, wherein the catalyst is formed in situ by reacting a neutral gold(I) complex of the formula 4

 L—Au—R' (4), wherein the ligand L represents a building block of the formula

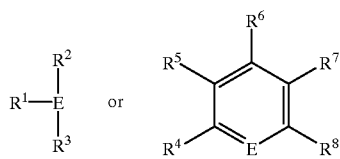

and

R$^1$, R$^2$ and R$^3$, each independently of the other, represent a substituted or unsubstituted aliphatic, cycloaliphatic, aromatic, heteroaromatic or araliphatic radical having from 1 to 30 carbon atoms which may be bridged and may optionally be attached to E via an oxygen atom or via a nitrogen atom;

E is phosphorus, arsenic or antimony;

R$^4$, R$^5$, R$^6$, R$^7$ and R$^8$ are each, independently, hydrogen or a substituted or unsubstituted aliphatic, cycloaliphatic, aromatic, heteroaromatic or araliphatic radical having from 1 to 30 carbon atoms, a corresponding alkoxy group or ester group, a nitro group, a cyano group or a halogen, and R' is alkyl, cycloalkyl, alkenyl, alkynyl, aralkyl or aryl, with a Brönsted acid HY, where Y is a weakly coordinating or non-coordinating anion, or with a Lewis acid.

9. A process as claimed in claim 1, wherein the catalyst is formed by dissociation of a stable gold(I) complex of the formula 3

 L—AuX (3), wherein the ligand L represents a building block of the formula

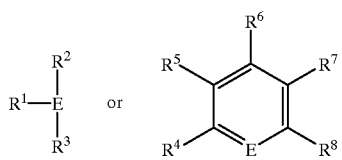

and

R$^1$, R$^2$ and R$^3$, each independently of the other, represent a substituted or unsubstituted aliphatic, cycloaliphatic, aromatic, heteroaromatic or araliphatic radical having from 1 to 30 carbon atoms which may be bridged and may optionally be attached to E via an oxygen atom or via a nitrogen atom;

E is phosphorus, arsenic or antimony;

R$^4$, R$^5$, R$^6$, R$^7$ and R$^8$ are each, independently, hydrogen or a substituted or unsubstituted aliphatic, cycloaliphatic, aromatic, heteroaromatic or araliphatic radical having from 1 to 30 carbon atoms, a corresponding alkoxy group or ester group, a nitro group, a cyano group or a halogen, and X is a radical which forms an anion in a polar medium.

* * * * *